US012125580B2

(12) United States Patent
Evans et al.

(10) Patent No.: US 12,125,580 B2
(45) Date of Patent: *Oct. 22, 2024

(54) SYSTEMS FOR MANAGING BIOPSY SPECIMENS

(71) Applicant: Leavitt Medical, Inc., Lehi, UT (US)

(72) Inventors: Mark S. Evans, Holliday, UT (US); Matthew O. Leavitt, Salt Lake City, UT (US); Jared L. Szymanski, Provo, UT (US); Michael Andrew Ivie, Orem, UT (US); Derek Brett Mann, Sandy, UT (US)

(73) Assignee: Leavitt Medical, Inc., Lehi, UT (US)

( * ) Notice: Subject to any disclaimer, the term of this patent is extended or adjusted under 35 U.S.C. 154(b) by 292 days.

This patent is subject to a terminal disclaimer.

(21) Appl. No.: 16/984,118

(22) Filed: Aug. 3, 2020

(65) Prior Publication Data

US 2020/0365241 A1 Nov. 19, 2020

Related U.S. Application Data

(63) Continuation of application No. 14/771,427, filed as application No. PCT/US2014/017230 on Feb. 19, 2014, now Pat. No. 10,734,099.

(Continued)

(51) Int. Cl.
*G16H 10/40* (2018.01)
*A61B 10/00* (2006.01)
(Continued)

(52) U.S. Cl.
CPC ............ *G16H 30/20* (2018.01); *A61B 10/00* (2013.01); *A61B 10/02* (2013.01); *G16H 10/40* (2018.01);
(Continued)

(58) Field of Classification Search
None
See application file for complete search history.

(56) References Cited

U.S. PATENT DOCUMENTS 8,645,167 B2 * 2/2014 Chirica ................. G16H 40/20
705/2
10,734,099 B2 8/2020 Evans et al.
(Continued)

FOREIGN PATENT DOCUMENTS

EP 2 958 497 A1 12/2015
JP 2006023977 A * 1/2006
(Continued)

OTHER PUBLICATIONS

Ly, Elodie & Piot, Olivier & Durlach, Anne & Bernard, Philippe & Manfait, Michel. "Differential diagnosis of cutaneous carcinomas by infrared spectral micro-imaging combined with pattern recognition." The Analyst. (2009). 134. 1208-14. 10.1039/b820998g. (Year: 2009).*

(Continued)

*Primary Examiner* — Rachel L. Porter
(74) *Attorney, Agent, or Firm* — Greenberg Traurig, LLP

(57) ABSTRACT

A system and method for on-site biopsy management. Patient information is retrieved through a biopsy system. A name of a patient, a biopsy type, and a site of the biopsy information are communicated to a user. Confirmations are received from the user through the biopsy system of the name of the patient, the biopsy type, and the site of the biopsy. A biopsy is associated with an identifier of a container securing the biopsy in response to receiving the confirmation. The biopsy information and the patient information is linked in the biopsy system. The linking is performed at a location the biopsy is performed.

15 Claims, 12 Drawing Sheets

Related U.S. Application Data

(60) Provisional application No. 61/776,780, filed on Mar. 12, 2013.

(51) Int. Cl.
| | | |
|---|---|---|
| *A61B 10/02* | (2006.01) | |
| *G06K 9/00* | (2022.01) | |
| *G16H 30/00* | (2018.01) | |
| *G16H 30/20* | (2018.01) | |
| *G06V 20/69* | (2022.01) | |
| *G16H 10/60* | (2018.01) | |
| *G16H 50/20* | (2018.01) | |
| *G16H 70/60* | (2018.01) | |

(52) U.S. Cl.
CPC .......... *G16H 30/00* (2018.01); *A61B 10/0096* (2013.01); *G06V 20/69* (2022.01); *G16H 10/60* (2018.01); *G16H 50/20* (2018.01); *G16H 70/60* (2018.01)

(56) References Cited

U.S. PATENT DOCUMENTS

| | | | | |
|---|---|---|---|---|
| 2004/0085443 | A1* | 5/2004 | Kallioniemi | G06V 20/693 348/135 |
| 2007/0136095 | A1 | 6/2007 | Weinstein | |
| 2008/0027756 | A1 | 1/2008 | Gabriel et al. | |
| 2008/0131362 | A1 | 6/2008 | Rousso et al. | |
| 2010/0167334 | A1* | 7/2010 | Williamson, IV | G16H 10/40 235/487 |
| 2011/0060766 | A1* | 3/2011 | Ehlke | G16H 30/00 715/810 |
| 2011/0238431 | A1 | 9/2011 | Cionni et al. | |
| 2012/0123223 | A1 | 5/2012 | Freeman et al. | |
| 2012/0290324 | A1 | 11/2012 | Ribbing et al. | |
| 2012/0328178 | A1* | 12/2012 | Remiszewski | G06T 11/60 382/133 |
| 2014/0135236 | A1 | 5/2014 | Musat | |
| 2014/0234895 | A1 | 8/2014 | Morales | |
| 2017/0220775 | A1* | 8/2017 | De La Torre-Bueno | G16H 70/60 |

FOREIGN PATENT DOCUMENTS

| | | | | |
|---|---|---|---|---|
| WO | 2010/151761 A2 | 12/2010 | | |
| WO | WO-2011091369 A1 * | 7/2011 | ......... | G01B 9/02044 |
| WO | WO-2013078419 A1 * | 5/2013 | ........... | G06F 17/148 |
| WO | 2014/130592 A1 | 8/2014 | | |

OTHER PUBLICATIONS

Non-Final Office Action received for U.S. Appl. No. 14/771,427 dated Apr. 5, 2018, 24 pages.
Final Office Action received for U.S. Appl. No. 14/771,427 dated Nov. 2, 2018, 27 pages.
Non-Final Office Action received for U.S. Appl. No. 14/771,427 dated Apr. 5, 2019, 28 pages.
Final Office Action received for U.S. Appl. No. 14/771,427 dated Oct. 7, 2019, 30 pages.
Notice of Allowance received for U.S. Appl. No. 14/771,427 dated Apr. 3, 2020, 30 pages.
International Search Report and Written Opinion received for PCT Application Serial No. PCT/US2014/017230 dated May 9, 2014, 9 pages.
International Preliminary Report on Patentability received for PCT Application Serial No. PCT/US2014/017230 dated Sep. 3, 2015, 8 pages.
Nochomovitz, Lucien E., "Gross Room and Specimen Handling", Modern Surgical Pathology, 2nd Edition, Chapter 1, 2009, pp. 3-12.
Extended European Search Report received for EP Patent Application Serial No. 14753641.1 dated Oct. 28, 2016, 5 pages.
Communication pursuant to Article 94(3) EPC received for EP Patent Application Serial No. 14753641.1 dated Dec. 5, 2017, 12 pages.

* cited by examiner

SYSTEMS FOR MANAGING BIOPSY SPECIMENS

CROSS-REFERENCE TO RELATED APPLICATIONS

This is a continuation of U.S. patent application Ser. No. 14/771,427, filed 28 Aug. 2015, titled "SYSTEM, METHOD, AND APPARATUS FOR DOCUMENTING AND MANAGING BIOPSY SPECIMENS AND PATIENT-SPECIFIC INFORMATION ON-SITE," which is a 371 of International Patent Application No. PCT/US2014/017230, filed 19 Feb. 2014, titled "SYSTEM, METHOD, AND APPARATUS FOR DOCUMENTING AND MANAGING BIOPSY SPECIMENS AND PATIENT-SPECIFIC INFORMATION ON-SITE," which claims the benefit of U.S. Provisional Patent Application Ser. No. 61/776,780, filed 20 Feb. 2013, titled "SYSTEM AND METHOD FOR DOCUMENTING AND MANAGING BIOPSY SPECIMENS AND PATIENT-SPECIFIC INFORMATION ON-SITE," the entire disclosure of each of which is incorporated herein by reference.

BACKGROUND

While the testing methodologies of blood, tissue, and genetic specimens are becoming increasingly sophisticated, the pre-analytic methods for handling these specimens and their accompanying clinical information remains archaic, subjecting patients to the potentially catastrophic consequences resulting from mislabeled specimens or inaccurate clinical information. The current state of the art acknowledges the primary importance of safely transporting specimens between the location where the biopsy or body fluid was taken, "the point of collection" (e.g. in a hospital room, a doctors clinic, endoscopy or surgical suite) and the laboratory.

Many existing solutions require multiple people at both sites to manually label and copy the critical clinical and patient information from papers that accompany each specimen into one or more computer databases, and to place tissues into individually hand-labeled formalin-filled specimen transport containers. Even in medical systems with strong information technology integration, the documentation of the physical characteristics of the specimens submitted for laboratory testing still relies on a verbal description of the tissue received. So, in addition to the safety risks brought on by the inevitable and occasional specimen mislabeling, existing solutions are markedly inefficient, leading to the unnecessary duplication of work, higher health-care costs, and poorer overall quality of care.

The present disclosure provides an integrated solution that automates manual tasks, eliminates duplicative efforts, and reduces the probability of errors during the process of taking and documenting multiple types of specimens.

SUMMARY

One embodiment provides for a specimen information system (SIS) comprising (i) a device to be used in the clinic where biopsy specimens are taken (clinic SIS); (ii) a device to be used in the lab where specimens are prepared and analyzed (lab SIS); and (iii) a software-based system that provides for collecting, calculating and managing biopsy-associated data.

In one embodiment, the clinic SIS is comprised of a housing for a portable computing device with a touch-sensitive screen and keyboard, a removable cover for the portable computer's keyboard, a digital camera, and one or more storage areas for magazines containing standard cassettes used for biopsy specimens. The keyboard can be revealed by removal of the cover to allow text and numeric data entry. With the cover closed, the workstation provides additional workspace for cassettes or other materials while allowing graphic data to be more conveniently entered using the touch screen.

Biopsy specimens taken by a physician or assistant are placed on the top cassette of the spring-loaded magazine. An image is taken that includes a bar code or other identifier associated with the cassette and the actual specimen being stored in the cassette. Images may be stored locally, uploaded via network facilities to other storage devices, or both. Images may be associated with data entered via the touch screen or keyboard, or drawn from other databases, including patient data that is then associated with the identifier of the cassette into which the biopsy specimen is placed. From that point forward all further actions taken with respect to the specimen on each cassette can be immediately identified by accessing the associated data.

The screen of the computing device may display a graphic image of the organ or anatomical area from which the specimen is taken, thereby providing an accurate association of the specimen with the specific location from which the biopsy is taken. Audio capabilities of the computer in the workstation allow audio feedback of data entered so that the operator and any others working as a team may receive verbal confirmation of data as it is entered without being distracted from other tasks.

In an alternative embodiment, a more portable version of the clinical workstation may comprise a single housing with an integrated camera, one or more cassette magazine storage areas, and a miniature single-board computer. The portable version may interface directly with a separate smart device, such as a tablet computer, that has its own graphic display, network connectivity, and that allows data entry via touch screen and/or keyboard input device. Using separate off-the-shelf components reduces the size and cost of the integrated system as well as making it more portable.

The lab SIS is a separate device used in the lab where specimens stored in the cassettes are processed and analyzed. The lab SIS comprises a holder that enables a paraffin embedded tissue cassette to easily slide under a fixed-mount camera, label reader, or other digital imaging device. The lab SIS captures the data imprinted upon the cassette, and based upon data previously associated with that specific cassette identifier directly prints any required number or variety of labels to be affixed to glass slides onto which sectioned portions of the specimens are placed for analysis, thereby assuring that the tissue on each slide continues to be associated with the specimen from that cassette, data entered via the clinic SIS when the specimen was taken, and all other associated data.

One embodiment provides a system and method for handling and documenting the physical characteristics of tissue biopsies. Patient-specific information may be entered or retrieved through a clinic specimen information system. A name of a patient, pertinent demographics, a procedure type, an exact anatomic site of the biopsy, and other information may be combined with the physical characteristics/descriptors of the tissue specimen and then communicated electronically to off-site users during or shortly after the completion of the procedure. Information regarding the clinic users and physicians is also associated with each specimen, based upon user authentication. The clinic SIS may provide auditory confirmation of patient name and/or biopsy type to the clinical user at the time of the procedure. A biopsy may be associated with a unique identifier of a container securing the biopsy in response to receiving the confirmation. The biopsy information and the patient information may be linked in the biopsy system. The linking of this data may be performed at the geographic location where the biopsy is performed. The patient clinical data and tissue-biopsy data may also be linked to any other type of physical specimen: genetic, blood, fluid, or other solid specimen data taken during the patient encounter.

The system provides for collecting, calculating, and managing biopsy-associated data. The system may include a computing device configured to access patient demographic and clinical information. The system may further include a scanning device (e.g. a camera or other digital imaging device) in communication with the computing device configured to image a biopsy. The biopsy may be placed into a container with a unique identifier, wherein the computing device may associate container identifier(s) with the patient information and with the scanner-collected/calculated data. The system may generate, from the image of the specimen other relevant data, including the dimensions of the specimens and the cross-section area of specimens, ensuring that the specimens are sufficiently representative to provide for accurate analysis. The clinic SIS and lab SIS may be integrated into the system used to perform these functions.

The clinic and lab SIS may also be integrated with whole slide image generated data, enabling comparison of the area of the tissue present on a glass slide with the area of tissue measurement calculated by the SIS at the time of the corresponding biopsy. The ratio of (whole slide image tissue area):(SIS-calculated tissue area) may be utilized by the histology lab to insure adequate depth of sectioning (i.e., adequate sampling of the tissue block).

The system includes a data management system in communication with the computing device and the scanner. The management system is configured to store and associate patient data and specimen data associated with each specific procedure only with specified laboratory's care providers, and only with specified clinical providers. The management system will enable multiple specimens and specimen types from a single clinical patient encounter to be associated together, and given an encounter (or "accession") number at the time and place of collection. The accession number may be represented as a bar-code or in other machine readable formats.

One embodiment of the device and or specimen information system could apply to pathology tissue laboratories or procedure rooms where larger, more complex examination and specimen sampling are required. In this embodiment, gross examination and documentation of the selected tissue samples taken from resection specimens can be accomplished using multiple cameras, linked into the SIS. The touch screen or other visual-based user interface systems (such as hands the hands free interactive system developed by Google Inc. —e.g. Google Glass) may be used to prompt the user through standard gross examination protocols, and based on user inputs, and other clinical information retrieved by the SIS (or one of its interfacing patient information systems) the computer may prompt the user to input specific observational data points associated with the specimen, clinical information and differential diagnostic considerations. The data from this gross examination embodiment may be associated with the SIS encounter information and then integrated with any form of patient, hospital, research, clinic, or laboratory database.

Utilizing the clinical history, symptoms, procedure indications, patient demographics, and procedural findings, the computational device and/or system may generate a list of potential diagnoses or pathologic explanations (i.e., differential diagnosis or DDx) that can be displayed during or shortly after the procedure, allowing the clinical providers to choose from a list of potential pathologic explanations for the patient's conditions. The data management system can associate and integrate this differential diagnostic data with whole slide imaging software and lab information system software to facilitate pathologic interpretation. This data may be integrated with artificial intelligence, or smart diagnostic algorithms, laying a framework for computer-aided interpretation/diagnostics.

BRIEF DESCRIPTION OF THE DRAWINGS

Illustrative embodiments are described in detail below with reference to the attached drawing figures, which are incorporated by reference herein and wherein.

DETAILED DESCRIPTION

Figure 1:
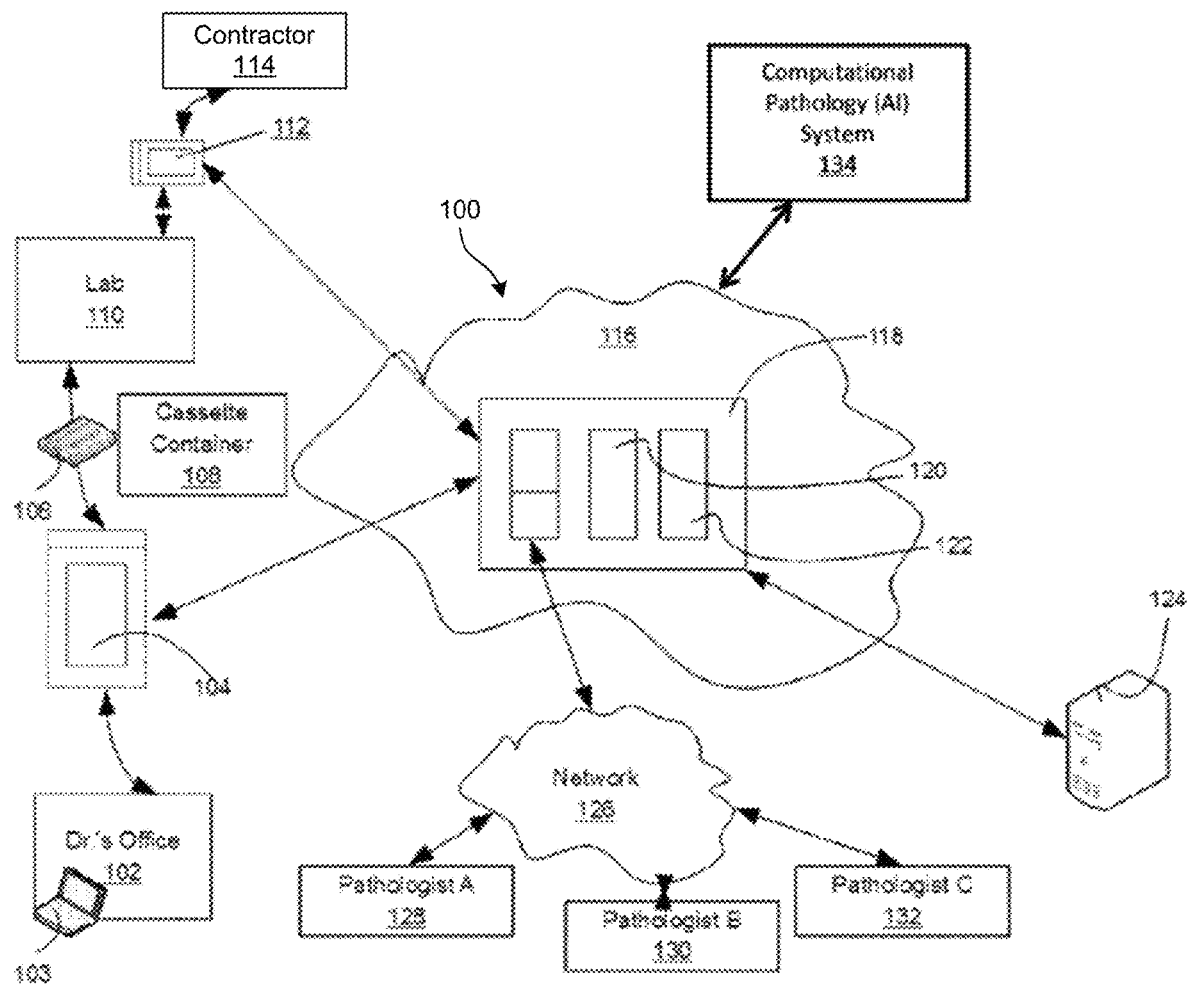
FIG. 1 is a pictorial representation of a digital pathology network in accordance with an illustrative embodiment.

The illustrative embodiments provide a system, method, network, and device(s) for processing tissue biopsies. A biopsy is a medical test most commonly performed by a medical professional by sampling cells, tissues, or a fluid specimen for examination. The specimen is tissue that is removed from a living patient generally to diagnose or document disease. The tissue may be visually and/or histochemically examined by a pathologist or other designated medical professional. The illustrative embodiments utilize digital imaging and cloud-based information technology to create a safer, more efficient process for specimen handling and for the documentation of associated clinical information and specific physical characteristics of the tissue at the time of the biopsy.

The illustrative embodiments describe an automated process for accessioning (i.e. the endowment of each specimen with a unique number or code that associates a specimen with a specific clinical encounter) and gross tissue examination (i.e. the standard documentation of the physical characteristics of the tissue submitted, to be included in a pathology report), which can be performed at the point and time of collection or in a secure cloud computing device, and further describes a system for electronically linking the specimen information to other clinically relevant patient information/specimen types (such as a blood sample or a genetic material harvest).

In the existing tissue and slide preparation processes performed in hospital and/or pathology labs there is considerable risk (and indeed a higher-than-acceptable frequency) for misdiagnosis due to mislabeling. The illustrative embodiments move part of the standard laboratory process to the location and time where specimen collection occurs. By eliminating unnecessary data transcription, tissue transfer and container labeling, the cost and risk of error is significantly reduced compared with any existing pre-analytic specimen handling process.

The illustrative embodiments enhance patient safety while increasing the efficiency and accuracy for production and processing of tissue biopsy slides. The illustrative embodiments may also prevent one of the most dangerous aspects of tissue processing which is mislabeling. For example, mislabeling errors may result in individuals or patients being incorrectly diagnosed, treated, or untreated with potentially disastrous consequences. Laboratories spend a significant amount of time and expense ensuring that patient specimen transport containers are labeled correctly and that when a tissue biopsy is placed into a processing cassette it is done properly. The illustrative embodiments are less susceptible to the frequently encountered misidentification errors that can result from the current practices of labeling processing cassettes, tissue transfer to these cassettes, gross-dictation, and transcription of the gross dictation. By removing redundant and extraneous steps from the process, the inefficiency and frequent errors associated with the current process are eliminated.

The illustrative embodiments provide hardware, software, and procedures that may be used and followed in whatever location a biopsy may be obtained or processed. Because the process is automated, the embodiments described herein are particularly well-suited for "point of specimen collection" processing.

FIG. 1 is a pictorial representation of a digital pathology network 100 in accordance with an illustrative embodiment. In one embodiment, the digital pathology network 100 may include a doctor's office 102, a computer 103, a scanner 104, cassette 106, cassette container 108, a lab 110, a scanner 112, a contractor 114, a network 116, a management system 118, a server 120, a database 122, a server 124, a network 126, pathologist A 128, pathologist B 130, and pathologist C 132. In addition, the system may be configured to communicate bi-directionally with a Computational Pathology System 134 for access to AI (artificial intelligence) expert system data and algorithms.

The doctor's office 102 represents the location, medical professional, and equipment that may be utilized to perform the biopsy. As used herein a user includes one or more medical professionals, people, or other individuals who operate the systems and devices of the digital pathology network 100. For example, the doctor's office 102 may represent a hospital, surgery, clinic, general practitioner's office, dental office, dermatologist office, genetic counselor's clinic, and so forth.

The digital pathology network 100 may include any number of laptop computers, tablets, wireless devices (e.g. iPhone, Android device, tablet, iPad, mp3 players, e-readers, etc.), networked device, or microprocessor-enabled devices all of which may be generically referred to hereafter as a "computer 103." The computer 103 may include any number of interfacing systems or peripherals, such as touch screens, displays, cameras, scanners, keyboards, mouse, trackball, and microphone and speakers for two-way communication with the user. For example, a computer 103 may be utilized by the doctor's office 102, lab 110, contractor 114, or pathologists A, B, and C 128, 130, and 132. For example, the contractor 114 may utilize a scanner similar to the scanner 104.

In addition, the digital pathology network 100 may communicate utilizing any number of public or private networks including communications service provider networks, cellular or data networks, virtual networks, wireless networks (e.g. WiFi, WiMAX, PCS, 3G, 4G, etc.), Ethernet networks, cloud networks, fiber optic networks, or so forth. The digital pathology network 100 may include a number of networks that are not shown. For example, the network 116 may represent a cloud network and network 126 may represent a private Ethernet network available to a hospital system.

The computer 103 may include an application, program, operating system, kernel, or set of instructions that is configured to record patient information and data, store and communicate images, and manage the initial generation of an electronic record associated with the specimen obtained during the biopsy. For example, the computer 103 may display a user interface utilized by the medical professional performing the biopsy, a medical assistant (e.g. nurse or practitioner assistant), or other user. In one embodiment, the computer 103 may be integrated with the scanner 104.

In one embodiment, prior to taking the biopsy, the computer 103 may prompt the user to enter the patient's information, such as name, address, insurance information, condition, and so forth. This information may be saved in an electronic record associated with the patient and the cassette 106. In another embodiment, the patient's information may be printed in a label that is attached to the cassette. Depending on the type of biopsy being performed, one or more cassette 106 may also be selected for receiving one or more specimens resulting from the biopsy.

The specimen may be placed in a cassette 106. The cassette 106 is a storage device for securing the biological sample. For example, the cassette 106 may be biopsy cassette produced by Leica, Tissue-Tek, Fisherbrand, (e.g. Histosette, Microsette, Unisette, Swingette, etc.). The cassette 106 may also represent any number of bottles, slides, boxes, or similar components.

The cassette 106 includes an identifier that is unique to each cassette 106. In one embodiment, the identifier is a bar code. However, the identifier may be or also include a serial number, QR code, radio frequency identification tag (RFID) tag, near field communications chip, or another similar identifier as known in the art. In one embodiment, the identifier of the cassette 106 is read by the scanner 104. The user may scan the bar code of the cassette 106 and associate the patient's name, birth date, body area, and specimen type with the bar code through a computer at the doctor's office 102. The scanner 104 may also be configured to perform document scanning.

In one embodiment, the cassette 106 and corresponding specimen may be scanned by the scanner 104. The scanner 104 may represent any number of scanning devices. In one embodiment, the scanner 104 may include a color camera and machine vision system. The scanner 104 may include one or more lights and cameras for visualizing the specimen. For example, the scanner 104 may utilize a number of different wavelengths (e.g. visible light, infrared, ultraviolet, X-ray, etc.) and images to visualize the specimen from one or more angles. In another embodiment, the scanner 104 may be configured to receive a cassette container 108 that secures a number of cassettes for analysis or transport.

In one embodiment, the digital pathology network 100 includes server side or client side software that provides a simple user interface, including the entry of patient demographics, critical clinical information, and a menu of tests that may be ordered from the point of care through the digital pathology network 100. For example, the user interface may be presented on the computer 103 or a mobile device utilized by the medical professional, such as a tablet computer communicating with a wireless data network of the Dr.'s office 102. In one embodiment, the management system 118 is a laboratory data portal 118. The data from the user interface may be electronically transferred to an encounter-specified file in a local or off-site server, such as server 120 or 124 or database 122 of the laboratory data portal.

The laboratory data portal 118 may be one or more devices or software systems utilized to enable, initiate, route, and manage communications and electronic records between one, or more communications and telephonic devices and systems. The laboratory data portal 118 may include one or more devices networked to manage the network 116. For example, the laboratory data portal 118 may include any number of servers, routers, switches, or advanced intelligent network devices. The network 116 sends and receives the electronic signals through any number of transmission mediums. The networks 116 and 126 may include various fiber optics, cables, transmission towers, antennas, dedicated devices, or other components for transmitting communications.

Files in the laboratory data portal 118 may be interfaced, integrated, or communicate with a lab information system or directly to an electronic medical record. The software utilized by the digital pathology network may include code that drives the user interface and manages the transfer of user input data to encounter-specific files within the laboratory data portal. The software may also drive the scanner 104 and manage the transfer of the data acquired by interface components into the same encounter-specific file within the laboratory data portal 118.

Utilizing existing solutions: (1) the documentation of the physical characteristics of tissue biopsies, (2) the assignment of a laboratory accession number, (3) the placing of the biopsy tissue into a uniquely labeled tissue processing cassette, and (4) the labeling, storage, and disposal of the formalin-filled biopsy transport container, and (5) all medical dictation and transcription involving the gross tissue specimen are all currently handled by the laboratory, requiring payment to the lab for these services.

While laboratories are well-equipped to handle specimens safely, and spend considerable time and resources ensuring patient safety, the fact is that tissue laboratories are temporally and geographically removed from the patient and staff who procured the biopsy, and as such must rely on written information on the specimen bottle and requisition paper to identify the source of the specimen. These added layers of complexity require redundant and extraneous steps to document the specimen source. Each of these steps is performed by a different person any one of which could make a simple mislabeling or transcription error, resulting in disastrous consequences for the patients. As a result, to be profitable, the current state of the art requires laboratories to recoup the cost of safely documenting and transferring tissue from a transport container into a tissue processing cassette.

In the illustrative embodiments, by placing the tissue biopsy directly and immediately into a tissue processing cassette 106 at the point of care and giving the cassette 106 and/or the cassette container 108 a unique identifier that is electronically-linked to the pertinent clinical information and specimen documentation, the costs and safety risks associated with the extra steps of transferring tissue from one container to another, manually entering data, and dictating and transcribing the specimen documentation are largely eliminated. In the existing solutions, the extraneous costs that result from tissue transfer and extraneous documentation comprises between 20-40% of the overall cost of producing a tissue biopsy slide. Conversely, the illustrative embodiments (including systems and methods) shift the work of documenting the submitted specimen away from the laboratory, and to those at the point of care, thereby disrupting the current economic model. By placing reimbursable lab services at the point of care, the illustrative embodiments enable those performing the services of specimen documentation and accessioning to be reimbursed for telepathology services at the fair market value for these services. As a result, a more efficient, safer, and economically viable and locally beneficial model may be implemented.

Figure 2:
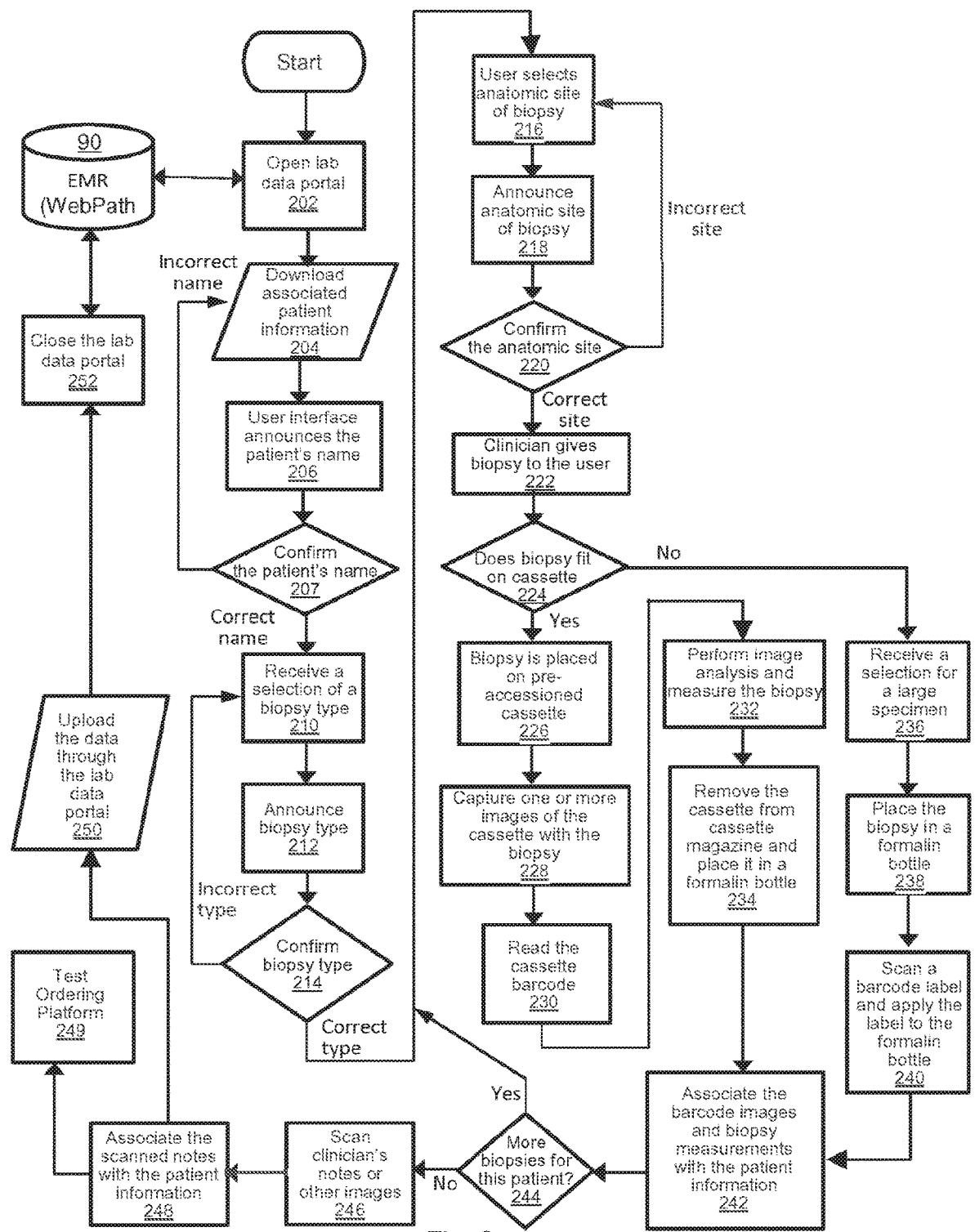
FIG. 2 is a flowchart of a process for managing biopsy specimens in accordance with an illustrative embodiment.

FIG. 2 is a flowchart of a process for managing biopsy specimens in accordance with an illustrative embodiment. The process of FIG. 2 may be implemented utilizing the system of FIG. 1 (including a user interface) or utilizing any number of computing, communications, or medical devices, equipment, networks, or systems. Various process steps may be performed based on user input (e.g. doctor, nurse, assistant, medical professional, etc.).

The process of FIG. 1 may begin by opening a laboratory data portal (LOP) (step 202). The LOP may be opened or accessed by a computing or communications device. In one embodiment, the LOP may be accessed through an Internet browser. The LOP may be accessed utilizing an add-in, application, extension, or other browser customization. In other embodiments, the computing device may execute a specific program or application to implement portions of the process automatically or in response to user input as are herein described. The LOP may include a secure connection to an EMR 90 or lab information system (LIS) with access limited to the data required for recording the biopsy samples. The secure connection may include usernames and passwords, account information, encryption, or so forth.

Next, a user may direct a computing device to download associated patient information from the electronic medical record database (EMR) through the LOP (step 204). The patient information may include, but is not limited to, the patient's name, age, gender, and any other important identifying information.

Next, a user interface of the computing device announces the patient's name (step 206). Next, the system confirms the patient's name is correct (step 208). During step 207, the system may wait for confirmation, feedback, or other input from the user through a user interface). The patient's name may be announced or displayed and confirmed textually, audibly, visibly, tactilely, or so forth.

If the announced name is not correct during step 208, the user initiates a new download of the associated patient information (step 204) which is again announced by the computing device (step 206) and confirmed (step 208). If the system determines the announced name is correct in step 208, the system receives a selection of a biopsy type (step 210). For example, the user interface may present a menu from which the user selects a biopsy type. The user may select default entries, such as lower GI, upper GI, or prostate or manual entries.

Next, the system announces the biopsy type (step 212). The announcement may be made by the user interface of the computing device as was previously described. Next, a determination is made whether the biopsy type is correct (step 214). The determination of step 214 is made based on feedback from the user based on the previous announcement of the biopsy type. If the biopsy type is not correct, once again the system presents a menu from which the user selects a biopsy type that is received by the system (step 210), the selection of the biopsy type is announced (step 212), and the biopsy type is confirmed (step 214)).

If the biopsy type is determined to be correct during step 214, the user selects an anatomic site of the biopsy (step 216). For example, the user may provide very specific details regarding the position and location of the biopsy. During step 214 the doctor, clinician, nurse, or other medical professional may take a biopsy, This step may apply equally to other types of specimens, including blood, fluid, or swab specimens, as well as a bar-coded genetic sample if appropriate.

Next, the system announces the anatomic site of the biopsy (step 218). The system then confirms the anatomic site is correct (step 220). If the anatomic site is not correct, steps 216-220 are repeated (e.g. the user must reselect the correct site with the system communicating the newly selected site for affirmative confirmation by the user).

Next, the clinician (or medical professional) takes a biopsy and gives it to the user (step 222). Next, a determination is made whether the biopsy fits in a cassette (step 224). If the biopsy is small enough to fit entirely in the cassette, the user places the biopsy into a pre-accessioned cassette (step 226). The cassette may have a number of features, such as a permanent label including a barcode, text, unique serial number, QR code, or other identifiers that may vary or be customized according to the user's or facility's needs. In another embodiment, the identifier may be a radio frequency identification (RFID) tag or near field communication (NFC) chip.

After the biopsy is placed in the pre-accessioned cassette, the user instructs the system to capture one or more images of the cassette with the biopsy (step 228). In one embodiment, the biopsy specimen and an identifier of the cassette may be imaged at the same time. However, in other embodiments, the images may be obtained separately.

After capturing the image, the system reads the barcode (step 230). The barcode may be read by a vision or scanning device of the system. Next, the system performs image analysis and the biopsy is measured (step 232). During step 232, the user and system may interact to measure and record the biopsy and a simple description of the specimen. The user then removes the cassette from the cassette magazine and places it in a formalin bottle (step 234). Any number of specimen containers may be utilized in place of a formalin bottle. In one embodiment, a single formalin transport container may hold several cassettes from multiple patients, and many be used to transport the cassettes to a designated laboratory.

If the biopsy does not fit in the cassette during step 224, the system receives a selection for a large specimen (step 236). For example, the system may present a user interface, menu, and option for selection a large specimen. Next, the biopsy is placed in a formalin bottle (step 238). Any number of large specimen containers may be utilized in place of a formalin bottle. Next, the system scans a barcode label and the label is applied to the formalin bottle (step 240). In one embodiment, the barcode sticker may be distributed to the clinic by the lab that processes the tissues. Larger specimens may be recorded at the location (i.e. bedside) but may have the other steps performed in the laboratory rather than at the location by the system.

Next, the computing device associates the barcode, images, and biopsy measurements, with the patient information (step 242). Next, a determination is made whether there are more biopsies for the patient (step 244). If there are more biopsies, the process returns again to step 216 and the corresponding steps.

In one embodiment, a medical professional may record an image or images of the biopsy sites (e.g. with an endoscopy camera). The system may scan the notes (handwritten or printed) or other images (step 246). For example, a document scanner may be utilized. At the end of the process, after all biopsies have been taken and recorded using the procedure or process outlined above, the system associates any scanned images and notes are associated with the patient information by the system (step 248). The system may also communicate with a test ordering platform (step 249) to add clinic-requested tests. Clinical images of the patient (such as a skin rash) taken with a conventional camera or cellphone camera may also be incorporated into the patient encounter and associated with any particular biopsy specimen.

In another embodiment, the LOP may be used as a test ordering platform, linking the orders from the clinic providers to individual specimens or patient encounters. The LOP test ordering platform may be used to request specific molecular/genetic tests that may or may not be dependent upon the interpretation of the associated specimens. The LOP test ordering platform may also include consent forms and patient identification verification forms which can be signed, or in some way click-verified by the patient at the time of, or shortly before or after the procedure. This test ordering data may be associated with genetic material through a uniquely bar-coded specimen label which may be physically attached to a buccal swab (such as has been used in commercially available tests like Know-Error-Strand Diagnostics) or a generic Vacutainer tube. The LOP associated test ordering platform may be used as a menu to display or suggest various molecular/genetic tests according to the patient's differential diagnosis. The prioritization of the various tests displayed may also be determined in part by the patient's insurance carrier. In one embodiment of the LOP associated test ordering platform, pre-approval for these tests may be granted by the patient's insurance carrier and transmitted electronically through a secure data transmission interface.

Upon completion of all other procedures the system uploads all data collected, including patient information, specimen data (including genetic or blood specimens), barcodes, cassette images, biopsy measurements, scanned images, notes (step 250) and additional test orders into the LOP. The LOP may then be closed (step 252).

When the laboratory personnel remove the cassettes from the respective transport containers, the personnel may scan the barcode and automatically access all the data that was uploaded to the EMR at the biopsy location. The cassettes may be managed and the biopsies analyzed without opening or relabeling the cassettes.

Figure 3:
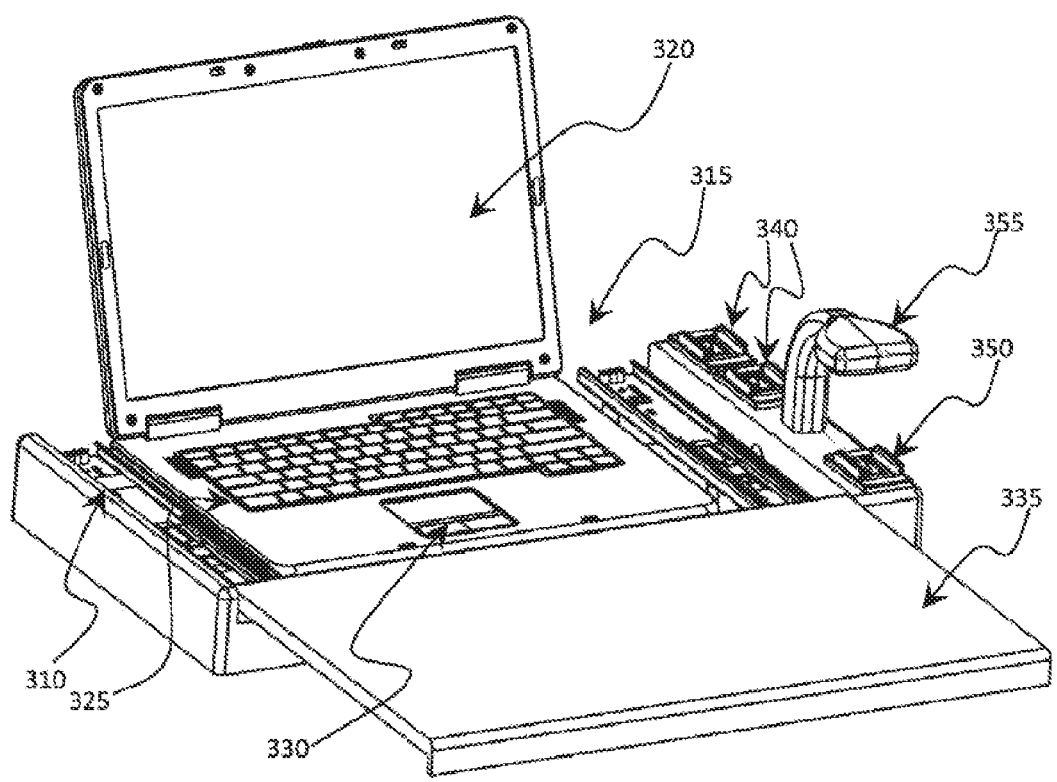
FIG. 3 is an isometric view of an integrated clinic SIS workstation with the work area open to expose the keyboard.

While discrete devices may be used at the collection point, an integrated device leverages the capabilities of the system and method described above at both the point of collection and in the laboratory provides significant advantages. FIG. 3. is an isometric view of an integrated clinic SIS workstation with the work area open, exposing the keyboard. The integrated clinic SIS workstation comprises a base 310 into which a portable computing device 315 may be placed, the computing device further comprising a screen 320, which may be a touch sensitive screen, a keyboard 325, and a mousepad or equivalent device 330.

The computing device would typically include an integrated power supply, memory, disk storage, an audio device with built-in speaker, a network port, and ports for connection of USB compatible devices. A sliding cover 335 may be moved horizontally along sliding groves 340 located on either side to the computing device, enabling the keyboard area to be replaced by a flat work service, while still providing access to computer-based functions via the touch screen 320.

On one side of the clinic SIS device one or more open bays 340 are provided for storage of biopsy cassette magazines. An additional bay provides a fixed location for the active cassette magazine 350 that will be used to hold specimens as they are taken. A digital imaging device 355 is located in a fixed mount positioned over the cassette magazine currently being used, the image device being connected to the computing device and controlled by means of keyboard, touchscreen, voice-activation or other instruction sequences. The digital imaging device records on a single image the cassette, including the accession identifier, such as a bar-code, and an image of the specimen itself.

The operator of the clinic SIS device may associate any desired data with the specimen and accession number being recorded, including patient information loaded from other databases or entered at the point of collection. The operator may associate additional information with the specimen by referencing graphical or text information on the touch screen. For example, the screen may depict an image of an internal organ such as the prostate gland, divided into multiple areas from which the clinician may take specimens. As the clinician takes a specimen and verbally indicated the point from which it is taken, the operator of the clinic SIS may identify the appropriate area by touching a diagram of the organ on the screen. The clinic SIS then uses the audio capabilities of the computing device to read back the name or other designation of the data selected. Accordingly, the clinician taking the specimen is able to confirm that the data has been accurately entered without being distracted from the specimen collection operation.

In another embodiment of the clinic SIS software, multiple specimens may be documented within a single cassette, using commercially available color-distinguishable, sectionable tissue arrays, such as the Biopsy Chip (Themis Pathology SRL, Romania). The clinic SIS software would allow multiple biopsy sites to be accurately and rapidly documented within the SIS platform, easing distinction of these separate specimens in the final glass slide/whole slide image.

In another embodiment of the clinic SIS device and software, non-tissue samples such as a bar-coded blood Vacutainer vile, or a bar-coded buccal swab sample (such as those utilized in the KnowError test) may be documented and associated with patient information and with corresponding tissue samples. Testing on these samples may be ordered by the clinic staff through the clinic SIS touch screen test ordering platform. For example: A young female patient undergoes a breast biopsy and informs the performing physician that she has a family history strong family history of breast cancer. The physician, recognizing the possibility that this patient may need to be tested for BRCA mutation collects germline DNA either by drawing blood or with a buccal swab. Consent for the test is obtained and input into the clinic SIS via a touch screen verification performed by the patient (such as by performing a finger signature on a small tablet). The physician may then order: If malignant, please reflex for BRCA testing. The data from this encounter, including the swab ID number (or blood vile ID number), the physician's order for BRCA testing, the patient's signed consent for the test are all uploaded along with the patient's tissue biopsy data to the LOP. This information can then be obtained in the histology lab via the lab SIS. The pathologist, having this information may, in the case of malignancy, then confirm the order for BRCA testing and send out/perform the genetic testing on the blood or buccal swab sample. The results from this test could then be returned to the clinic via the SIS-LIS interface.

As each specimen is recorded from its position on top of the active cassette magazine 350, the cassette itself removed from the active cassette magazine by sliding it out of the magazine. The recorded cassette may then be placed in an appropriate preservative solution. A new cassette is brought into position by the spring-loaded mechanism in the cassette magazine, facilitating rapid and accurate recording of multiple specimens. When a cassette magazine is empty, a new one from the built-in magazine storage bays may be quickly placed in the active magazine bay for immediate continued use. The cassette dispensers and magazine bays are formed complementary to one another so as to only allow a magazine to be placed into the bay with its bar-coded cassettes situated at the proper distance and angle from the fixed-camera/scanning device. Any number of recorded cassettes may be safely stored in a single container of preservative as each is identified with the appropriate accession number and all associated data and images have been duly recorded and associated with that number by the system.

In one embodiment of the clinic SIS device could be modified for use in the pathology tissue laboratory (ie. "gross room), or in hospital procedure rooms where larger, more complex examination and specimen sampling are required. In this embodiment, gross examination and documentation of the selected tissue samples taken from resection specimens can be accomplished using multiple cameras, linked into the SIS. The touch screen or other visual-based user interface systems (such as hands the hands free interactive system developed by Google Inc., e.g., Google Glass) may be used to prompt the user using prompts that are designed around standard gross examination protocols, and based on user inputs, and other clinical information retrieved by the SIS (or one of its interfacing patient information systems) the computer may prompt the user to input specific observational data associated with the specimen, clinical information and differential diagnostic considerations. For example, a skin biopsy could be grossly examined using elements of the following procedure. 1) Patient information linked to the specimen is retrieved or input. 2) The specimen container with label information is photographed/read under one camera driven by the SIS touch screen interface. 3) The intact gross specimen is photographed and measured on a solid background (blue or green) mat, enabling automatic measurement of the specimen dimensions. 4) The specimen is inked according to a standard inking protocol that is stated and then confirmed by the user on the touch screen. 5) The specimen is serially sectioned, and another photograph is taken of the sectioned specimen. 6) The samples submitted for microscopic examination are then loaded one by one into the a uniquely identified cassette and the exact site (e.g., "Right cheek 12-3 o'clock peripheral margin") may be associated with the submitted sample by touching the prompt on the screen. The data from this gross examination embodiment may be associated with the SIS encounter information and then integrated with any form of patient, hospital, research, clinic, or laboratory database.

Figure 4:
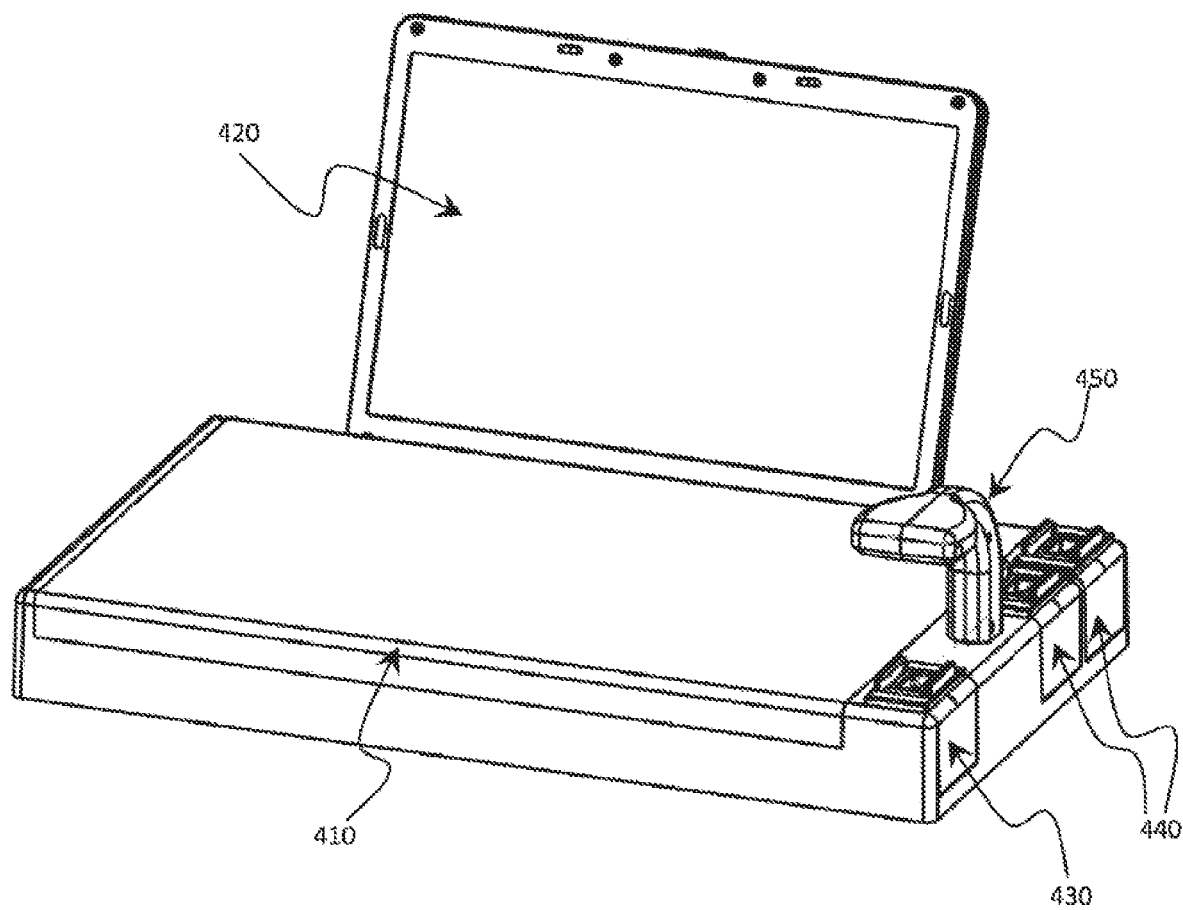
FIG. 4 is an isometric view of an integrated clinic SIS workstation with the work area closed and with spare cassettes loaded in storage areas.

FIG. 4 depicts an isometric view of the integrated clinic SIS with the cover in the closed position 410 and with spare cassette magazines 420 loaded in the empty magazine bays. The screen 420 remains visible for data input via the touch screen functionality. The active cassette magazine 430, spare magazines 440, and digital imaging device 450 remain accessible for use with the cover in work-space position. This configuration allows the majority of space taken by the clinic CIS to double as a workspace and storage space without inferring in any way with the functionality of the device and system. When the clinic SIS not in use, the cover 410 may be closed after the computing device screen is lowered for secure storage.

Figure 5:
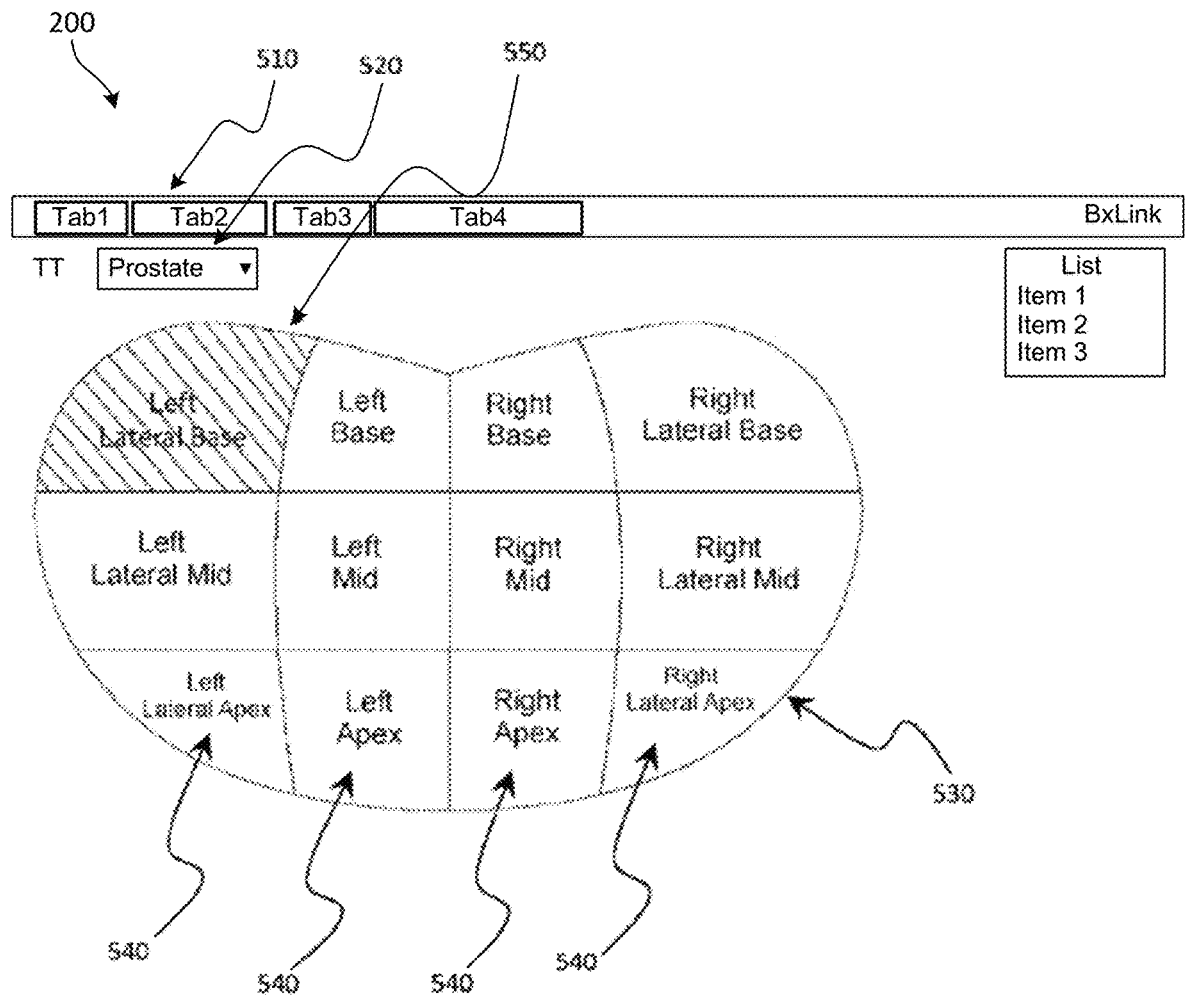
FIG. 5 is an exemplary screen shot from the graphic interface of the SIS.

FIG. 5 is a sample screen shot that may be used to provide graphical input for recording biopsy specimens taking using the system, in this example, from the prostate. The graphic interface may be displayed within a windowing environment 510 as known in the art. A drop-down menu 520 facilitates the selection of the organ or anatomical area from which tissue specimens will be taken. Upon selecting the desired organ or anatomical area, a graphic display 530 is presented showing the standard locations within the organ from which multiple specimens may be taken 540. As the medical professional taking the specimens orally identifies the area from which a specimen is being taken the SIS operator confirms that area by referencing the appropriate position on the touch screen. The SIS device may orally repeat back the location using pre-recorded audio files or text-to-speech conversion to allow the professional taking the specimen to receive confirmation, thus avoiding errors.

When the SIS operator presses the appropriate area on the touch screen, an image is captured and stored in association with that area designation. The graphic display may darken, change color, or otherwise indicate that specimen from that area has been taken and it's cassette imaged, associating the specimen location and image with the pre-accessioned identifier such as a bar code on the tissue cassette. Multiple samples may be taken from the same area if the medical professional deems it appropriate.

In the example illustrated, it is common practice for a prostate examination to take one or more tissue samples from twelve different areas of that gland, each of which is identified by standard medical nomenclature 5.

Figure 6:
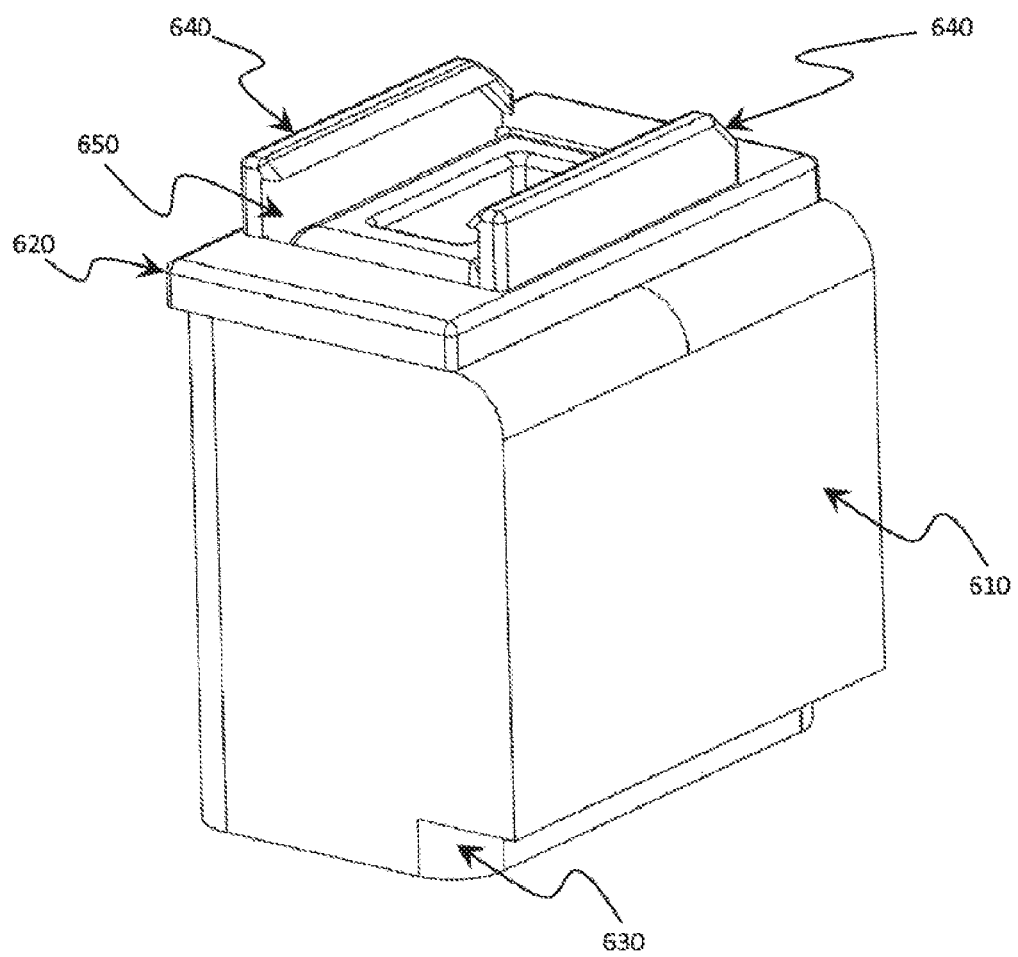
FIG. 6 is an isometric view of the cassette magazine used in conjunction with the clinic SIS devices.

FIG. 6 is an isometric view of one embodiment of the cassette magazine used in conjunction with the clinic SIS. The magazine comprises a housing 610 into which a predetermined number of standard specimen cassettes can be loaded by removing the cover assembly 620. An indentation 630 at the base of the cassette magazine allows the magazine to sit securely within the magazine storage bays which, in the case of the bay for the active magazine, further ensures that the specimen and cassette being photographed are held stationary while a digital image is taken.

Internal springs push a stack of cassettes upward such that the uppermost cassette is pressed against flanges 640 that are shaped to hold a predetermined size and shape of cassette in place. One end of the magazine upper assembly is left open 650 so that a cassette may be readily removed by sliding it out the open end, at which time the next cassette in stack is pushed upward in a manner similar to that used in brick-like candy pellet dispensers.

Figure 7:
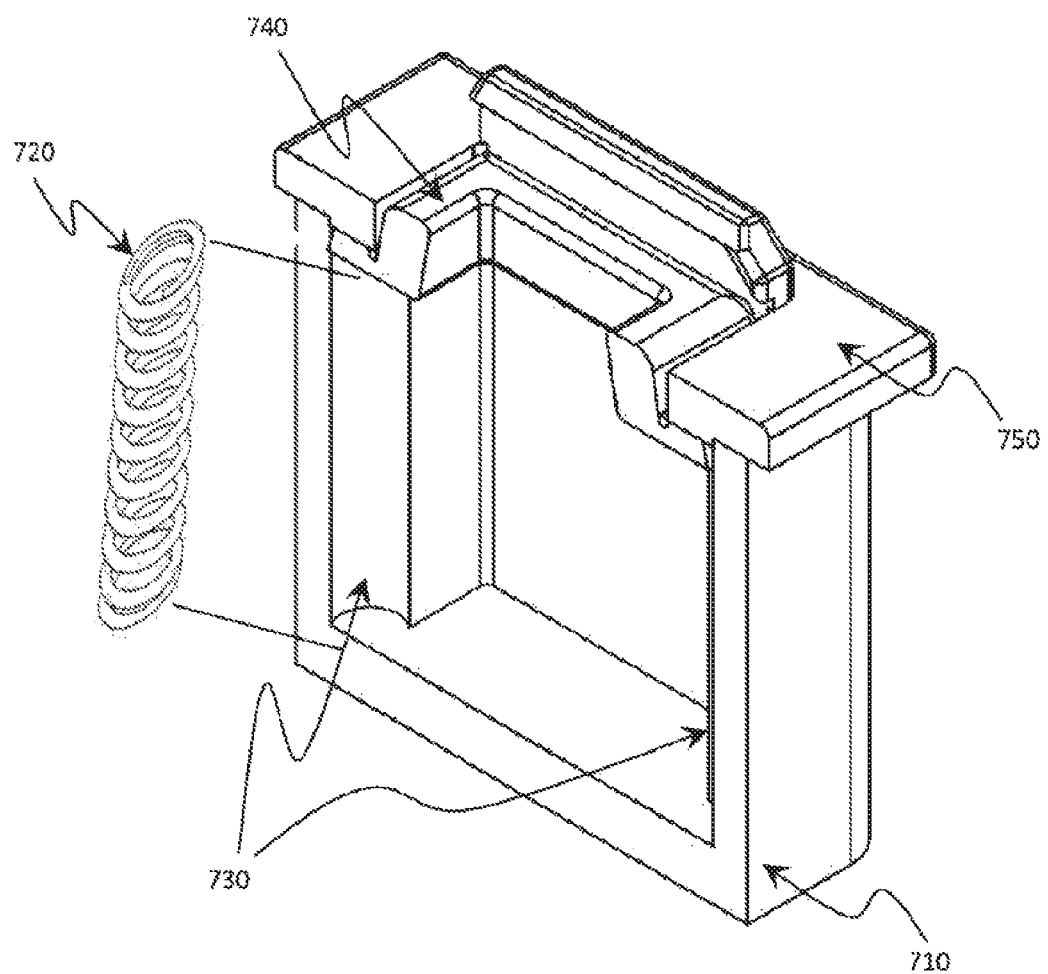
FIG. 7 is a cutaway view of the cassette magazine used in conjunction with the clinic SIS devices.

FIG. 7 is a cutaway view of one embodiment of the cassette magazine, showing one-half of the magazine housing 710. Inside the base of the cassette magazine, two coil springs (one shown) 720 are housed in cylindrical channels 730 on either side of the magazine. A cassette pusher 740, configured to accommodate the size and shape of the tissue cassettes being used, moves freely up and down within the cylindrical channels and the hollow interior of the cassette magazine housing. The compression of the coil springs pressing upward on the stack of cassettes moves each cassette to the top of the stack and against the top housing 650 in turn as the cassettes are loaded with tissue specimens and removed from the magazine.

Figure 8:
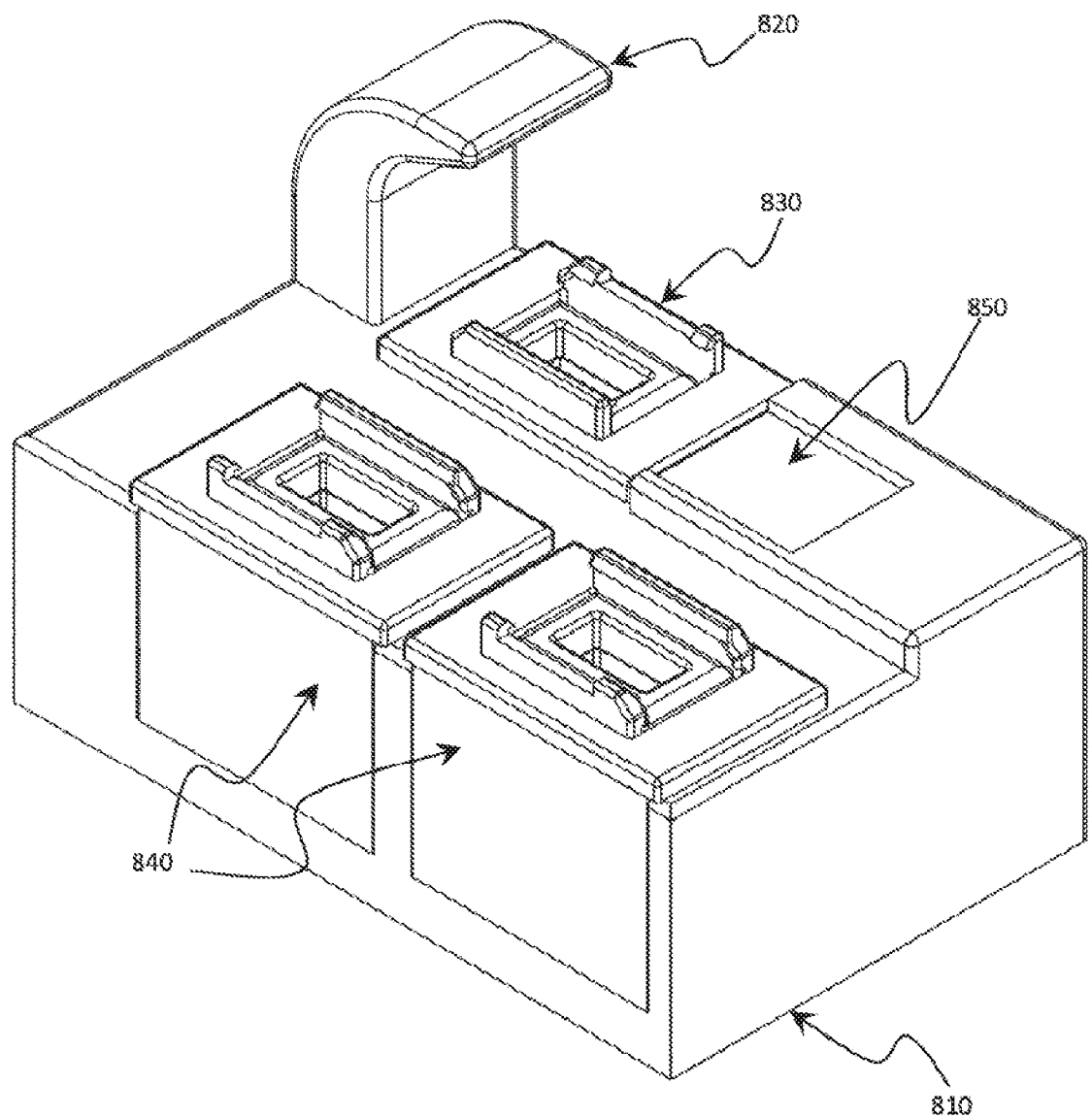
FIG. 8 is an isometric view of the portable version of the clinic SIS device with integrated single-board computer.

FIG. 8 depicts an isometric view of one embodiment of the portable clinic SIS device. A housing 810 is provided to accommodate the digital imaging device 820, which is located in a fixed position above the active cassette magazine 830. Additional magazine bays are provided for two additional cassette magazines 840. A holding tray 850, sized in accordance with the tissue cassettes being used, is provided to securely position a cassette removed from the active magazine temporarily, so that a lid may be placed on the cassette. The holding tray enables the operator to securely position a lid on the most recently loaded cassette using only one hand facilitating fully portable use of the device.

The portable clinic SIS, while being sufficiently small to be moved about with one hand, is sufficiently large to accommodate a single-board computer such as the credit-card sized Raspberry Pi or Arduino boards. Such boards typically include a central processing unit, graphics processing unit, dedicated memory, audio capability, a bus for communication with other compatible modules designed for use with the same system, as well as standard ports such as USB, network, digital camera CSI, video out, and audio. Programming can be preloaded for operation of the single-board computer or provided on a memory device such as a thumb drive or flash memory cards. Single-board computer power requirements are such that they may be powered by a small transformer or by internal batteries for added portability.

The portable clinic SIS device may be readily configured to operate in conjunction with other input or display devices, including the touch screen display of a smart device such as a telephone or tablet. Alternatively, the portable clinic SIS device may communicate with the device through programs that run natively on such devices, as is known in the art. By combining the smaller portable device with standard external devices which are also portable, the entire systems is highly portable and can be set up in a matter of minutes at any desired point of collection.

Figure 9:
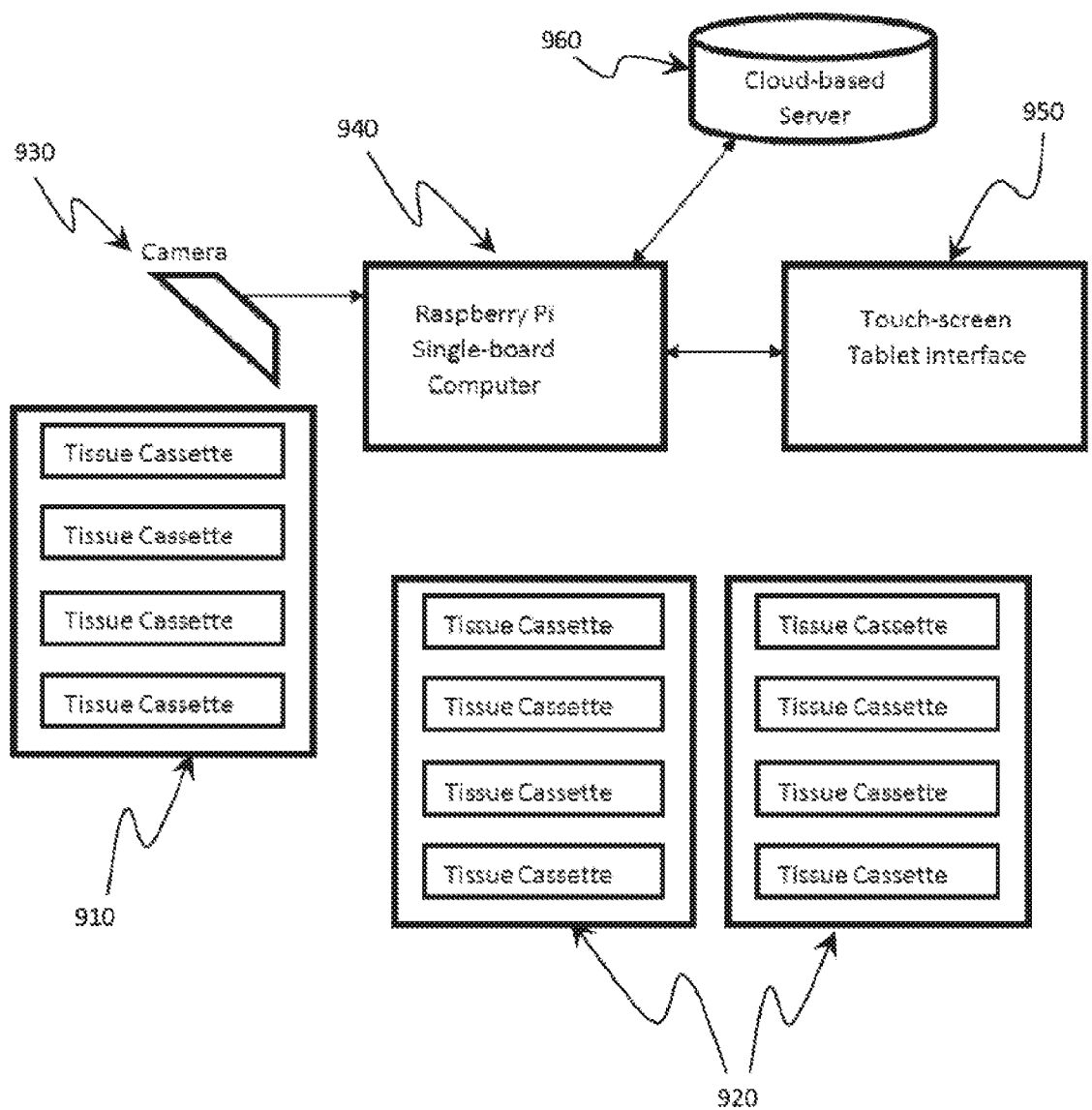
FIG. 9 is a block diagram illustrating the functionality of the portable version of the clinic SIS device.

FIG. 9 is a schematic block diagram of the elements of the portable clinic SIS device that accommodates, as described herein, an active tissue cassette magazine 910 as well as one or more spare tissue cassette magazines 920. The digital imaging device 930 is positioned over the active tissue cassette and communicates with the single board computer, in illustrated embodiment a Raspberry Pie device 940, via a standard digital camera interface. The single board computer is controlled by means of a touch screen device 950, which communicates bidirectional with the single-board computer.

Commands may be entered by means of a graphic or text interface display on the touch screen interface. Alternatively, a keyboard compatible with the touch-screen interface device may be added. External keyboards compatible with popular tablet devices based on Apple Computer's iOS operating system or on the Android operating system are readily available. Commands generated through the touch-screen interface device indicate the nature and location of the specimen being taken, as described above, and trigger the capture of a digital image. The image may be stored locally and/or also automatically uploaded to a cloud-based server via wired or wireless network and associated with other relevant data relating to the patient or the procedure. Immediate storage of the relevant data is later retrieved during the analysis of specimens thus insuring that no transcription errors result in misidentification of patents, tissue specimens, or other critical elements.

After tissue specimens are taken and placed in a tissue cassette, the cassettes are placed in a container containing a preservative solution. Any number of cassettes may be preserved together based on the accession identifiers that are recorded and associated with each cassette. Upon arrival at a lab for analysis, the preserved specimens are typically removed from cassette and embedded in wax on the back of the cassette following which they can be sampled using a microtome or other sectioning device as known in the art. Thus, during the analysis process, the sample sections taken from a specimen continue to be associated with the accession identifier from the original cassette.

Figure 10:
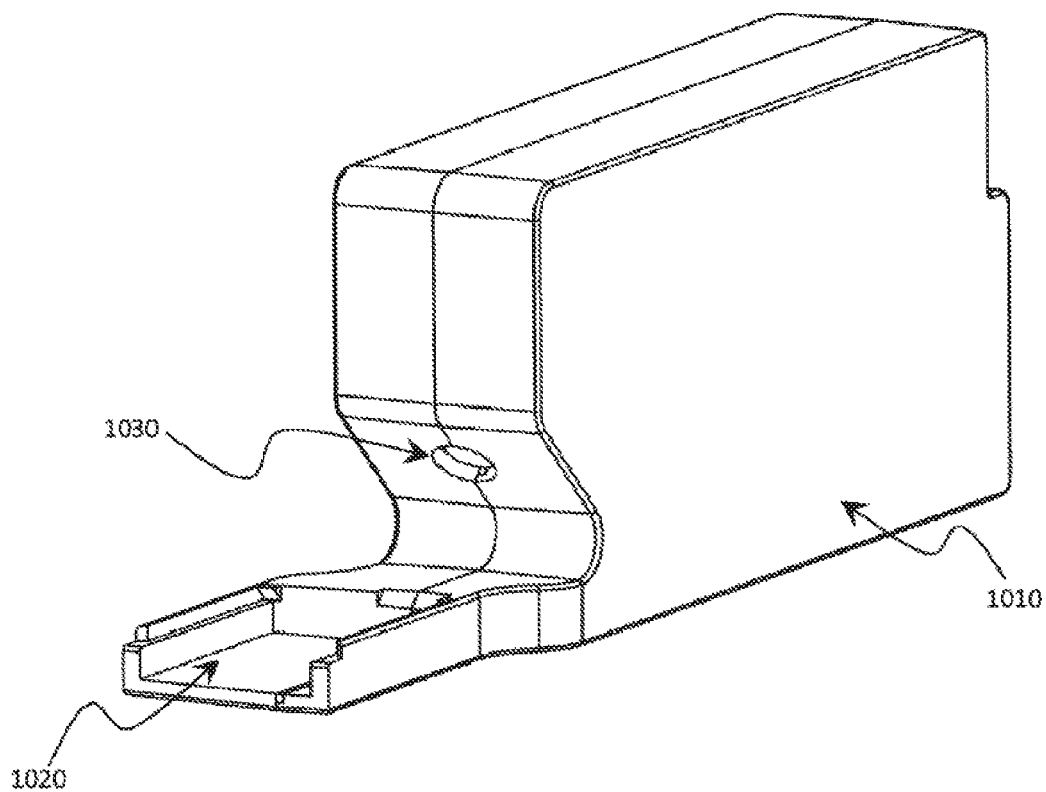
FIG. 10 is an isometric front view of the lab SIS device.

FIG. 10 is an isometric view of the lab SIS device. The lab SIS device is a limited purpose device to be used in the lab where the specimen will be sectioned and analyzed. The lab device works in conjunction with the clinic SIS device that was earlier used at the point of specimen collection. The lab SIS device comprises a housing 1010 that includes a cassette receiver 1020 and an integrated imaging device 1030.

Internally, the housing comprises a single-board computer, as described above in connection with the portable version of the clinic SIS device, that can read or duplicate the accession number or code and can print directly to a label printer. The lab SIS device is designed to operate as headless device, as known in the art. That is, the device does not require a monitor, keyboard, mouse or other display or input accessory. The lab SIS device can be configured to send raw data directly to a printer by means of a standard network connection or other standard communication protocols, thus creating text or graphic images on labels without the need of a print driver.

Figure 11:
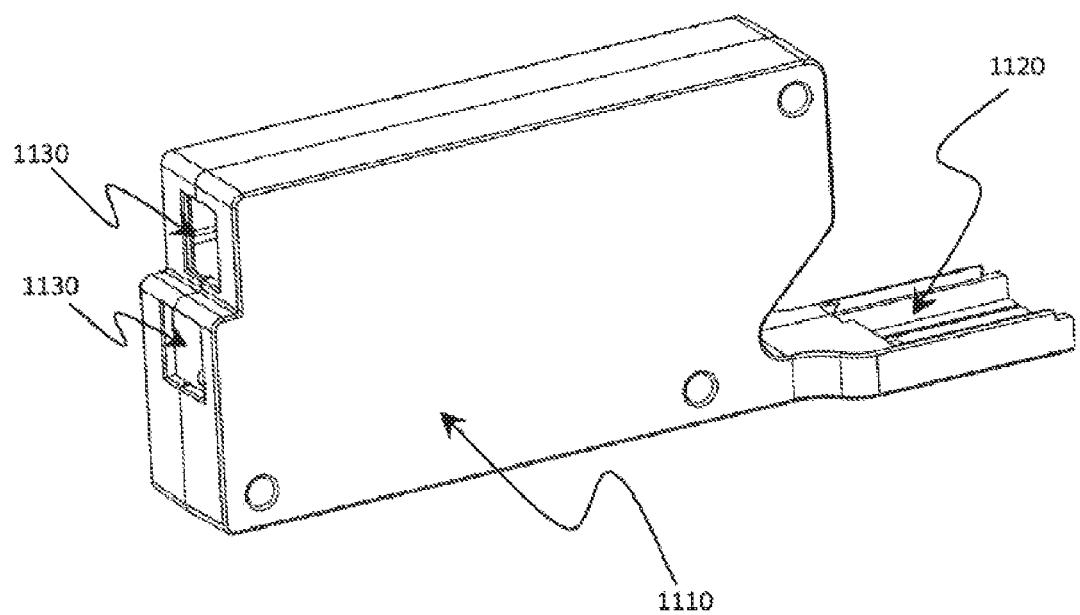
FIG. 11 is an isometric rear view of the lab SIS device.

In one embodiment, the lab SIS device prints labels by sending binary data directly to a label printer using a standard computer network connection. FIG. 11 is an isometric view of the rear of the lab SIS device showing the housing and the holding tray 1120 that positions the cassette with respect to the imaging device 1030. One or more network ports 1130 are positioned on the rear of the device to allow easy manipulation of the device while it is connected to a printer and/or a router or switch allowing direct communication with the cloud storage associated with the system. In one embodiment, the connectivity with the label printing device uses standard RJ45 female network jacks and a standard computer network cables to interface with the printer and with the internet for access to the cloud storage system.

A specimen cassette with the wax embedded specimen is analyzed by sectioning using a microtome or other device to prepare a thin section for viewing under a microscope by the pathologist or other lab professional. Typically, a number of sections are taken to ensure evaluation of the entire specimen and to ensure that the specimen has been examined to the proper depth or at multiple depths.

The lab SIS device allows insertion of a specimen cassette into the device receiver each time a section is taken. Rather than using a switch, the lab SIS digital imaging device continuously monitors the receiver. When it detects an accession identifier it knows that a cassette has been inserted and commencing processing the data. The imaging system reads the accession identifier associated with that cassette in the form of text, bar code or other means, downloads pertinent data associated with that cassette from the cloud server, and prints a label that duplicates the accession identifier in addition adding a sequential number and any other instructions associated with the specimen. The label is sized appropriately for inclusion on standard glass slides used in pathology labs. This facilitates the preparation of a sequential set of numbered slides all of which are associated with the specimen from a single cassette. The analysis or any slide may then be readily associated with the specimen from which it was taken and all other data associated with accession identifier of that specimen, including patient data and information generated at the point of collection. As a headless device, the lab SIS device requires no accessory components other than the label printer, and can be conveniently used in a lab as specimens are sectioned and mounted on slides.

In another embodiment, the lab SIS device can be wired or linked wirelessly to a monitor or other interactive electronic visualization device (such as that developed by Google, e.g., Google Glass), enabling either clinic or pathologist generated orders to be taken and executed in the lab.

As a specimen is sectioned and repeatedly inserted into the lab SIS device's receiver, the linear dimensions and the area of each section may be computed automatically, as described above in connection with clinic SIS device. The area of each section may then be expressed as a percentage of the total specimen area or size and associated with criteria that allow verification that the section is sufficiently representative for accurate analysis. For example, such percentage comparison aids in determining when the sectioning has reached sufficient depth into the specimen to ensure that conditions being tested, if present, will be visible on the slide.

Figure 12:
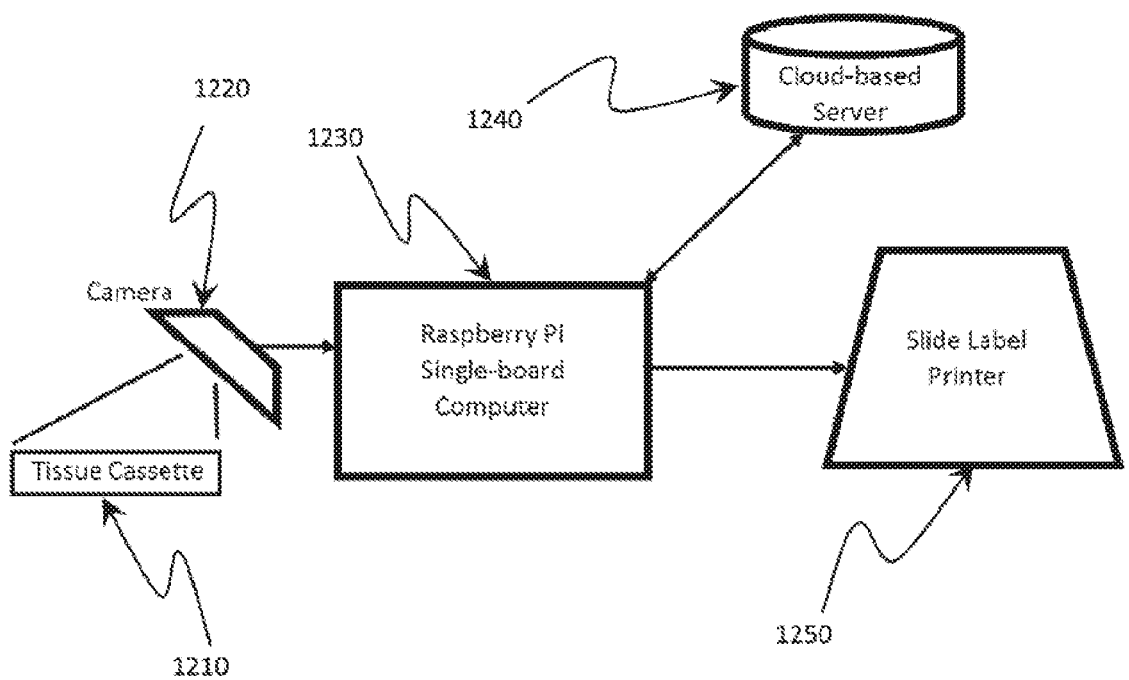
FIG. 12 is a block diagram illustrating the functionality of the lab SIS device.

FIG. 12 is a schematic block diagram of the components comprising the lab SIS device. A cassette with a wax-embedded tissue sample in a tissue cassette 1210 is placed in the receiver where it is positioned under the digital imaging device 1220 that, in turn, communicates the image data to the single-board computer 1230. The text or image accession information is processed in the single-board computer capturing the accession identifier, typically in the form of a bar code. The accession identifier captured by the lab SIS can be immediately uploaded to the data storage in the system's cloud 1240 via the internet where it is associated with all other information associated with the patient, procedure, and other relevant data captured at all prior stages that comprise the system and method.

From that captured data, the lab device can receive any pre-determined slide-ordering instructions requested to be carried out in connection with processing or analyzing the specimen. A key example is the requirement to stain different specimens differently to facilitate accurate analysis. Under the current state of the art, staining instructions must either be independently determined by contacting the appropriate technician or physician each time a slide is prepared, or else resort to a default standard.

Using the described system and method, different staining protocols may be associated with a given specimen. The clinic at which the specimen is taken may use differential diagnosis to determine the appropriate stain instructions to be associated with the specimen and include that data at the point of collection using the clinic SIS device. For example, if the specimen biopsy is taken for the purpose of ascertaining the existence of a gastric ulcer, the differential diagnosis will indicate the appropriate stain to test for the presence of the *H. pylori* bacterium. The staining instructions are then associated with that specimen and available at the lab via the lab SIS device.

Upon retrieval of stain information or other slide-ordering instructions, the single-board computer creates a binary file that is passed directly to the slide label printer 1250, the label providing the accession number of the tissue specimen, the numerical identifier of the slide in a series taken from a single specimen, and any stain requirements or other instructions for preparation of the slide.

The single board computer may also feed the stain/test order data to a digital order board, computer screen or other interactive electronic visualization tool to display the incoming orders. These orders may include requests from providers (pathologists or clinicians) for esoteric tests. These orders may also generate automated instructions to guide those handling fewer routine tests to handle them in an appropriate manner. For example: A pathologist may recognize the need to order BRAF V600e testing on a specimen containing colon, thyroid, or skin cancer. He or she could then place the order in the LOP from his desktop computer by choosing from a menu of providers that offer that test. The order would be placed for the particular slide containing the cancer. The LOP could then associate the slide data with the appropriate tissue block and display the request for the corresponding tissue block and the instructions for send out to the particular lab of choice. If, for example, the send-out instructions require the cutting of unstained slides, then the pathologist requested test would also automatically generate an unstained slide order to the single board computer (via the lab SIS). Upon scanning the retrieved block, the slide label printer would print out a label showing order-appropriate information, such as: Patient name, accession number, and send out test order. These same test order embodiments could be initiated at the point of specimen collection, around the time or following the procedure.

The previous detailed description is of a small number of embodiments for implementing the invention and is not intended to be limiting in scope. The following claims set forth a number of the embodiments of the invention disclosed with greater particularity.

What is claimed is:

1. A system for managing biopsies, the system comprising:
    a first computing device configured to access patient information;
    a first digital imaging device, including at least one of a first camera and a first scanner, positioned at a location of retrieval of a biopsy specimen from a patient, wherein the first digital imaging device is in communication with the first computing device and is configured to capture at least one first image of the biopsy specimen at the location of retrieval of the biopsy specimen from the patient prior to fixation of the biopsy specimen and prior to transporting the biopsy specimen to a laboratory for processing to provide the first image of the biopsy specimen in a pre-processed state, wherein the biopsy specimen is placed in a container including an identifier, and wherein the identifier is associated with the patient information by the first digital imaging device;
    a second digital imaging device, including at least one of a second camera and a second scanner, positioned in the laboratory, wherein the second digital imaging device is configured to capture at least one second image of the biopsy specimen in the laboratory after fixation of the biopsy specimen to provide the second image in a post-processed state;
    a computational pathology system, including a second computing device, for providing image analysis of the first image and the second image of the biopsy specimen, for providing automatic biopsy area measurements based on the first image and the second image of the biopsy specimen to determine a first area of the tissue present in the first image and a second area of the tissue present in the second image, and for comparing the first area with the second area; and
    a management system, including a third computing device, in communication with the first computing device, the first digital imaging device, the second digital imaging device, and the computational pathology system, wherein the management system is configured to store the patient information, procedure information, and specimen information associated with the procedure, wherein:
    the specimen information includes at least the at least one first captured image, the at least one second captured image, the image analysis, the biopsy area measurements, and the comparison of the first area and the second area;
    at least a portion of the specimen information is generated by one or more providers; and
    the patient information, procedure information, and specimen information are available from the management system for access by laboratory personnel.

2. The system of claim 1, wherein the patient information includes an electronic medical record.

3. The system of claim 1, wherein the computational pathology system is further configured to provide one or more differential diagnoses based at least in part on the first image of the biopsy specimen.

4. The system of claim 1, wherein the management system includes one or more servers configured to provide a lab data portal (LDP).

5. The system of claim 1, wherein the at least one first image includes one or more digital photographs associated with the biopsy specimen that are linked with the patient information.

6. The system of claim 1, wherein the first computing device communicates a name of a patient, a biopsy type, and a site of the biopsy as biopsy information to a user and receives confirmations from the user through a biopsy system of the name of the patient, the biopsy type, and the site of the biopsy.

7. The system of claim 6, wherein the communications are received audibly by the user in response to user selections.

8. The system of claim 1, wherein the management system is accessed through a cloud network.

9. The system of claim 1, wherein the first digital imaging device is configured to capture the first image of the biopsy specimen positioned on or in a color-distinguishable, sectionable tissue holder within the container.

10. The system of claim 1, wherein the first computing device is further configured to link the patient information with the specimen information.

11. The system of claim 1, wherein at least one of the first computing device, the computational pathology system, or the management system is further configured to link data related to another, different physical specimen from the patient to the specimen information related to the biopsy specimen retrieved from the patient.

12. The system of claim 1, wherein the second image comprises a whole slide image.

13. The system of claim 1, wherein the image analysis of the first image of the biopsy specimen provided by the computational pathology system includes performing automated gross tissue examination of the biopsy specimen.

14. The system of claim 13, wherein performing the automated gross tissue examination includes automatically measuring the biopsy specimen dimensions from the first image of the biopsy specimen.

15. A system for managing biopsies, the system comprising:
- a first computing device configured to access patient information;
- a first digital imaging device including at least one of a first camera and a first scanner. positioned at a location of retrieval of a biopsy specimen from a patient, wherein the first digital imaging device is in communication with the first computing device and is configured to capture at least one first image of the biopsy specimen at the location of retrieval of the biopsy specimen from the patient prior to fixation of the biopsy specimen and prior to transporting the biopsy specimen to a laboratory for processing to provide the first image of the biopsy specimen in a pre-processed state;
- a second digital imaging device including at least one of a second camera and a second scanner, positioned in the laboratory, wherein the second digital imaging device is configured to capture at least one second image of the biopsy specimen in the laboratory after fixation of the biopsy specimen to provide the second image in a post-processed state;
- a computational pathology system including a second computing device configured for performing image analysis of the first image and of the second image of the biopsy specimen, wherein the image analysis includes:
  performing automatic biopsy area measurements based on the first image and the second image of the biopsy specimen to determine a first area of the tissue present in the first image and a second area of the tissue present in the second image; and
  comparing the first area and the second area; and
- a management system including a third computing device in communication with the first computing device, the first digital imaging device, the second digital imaging device, and the computational pathology system, wherein the management system is configured to store the patient information, the first image, the second image, the biopsy area measurements, and the comparison of the first area and the second area, wherein the patient information, the first image, the second image, the biopsy area measurements, and the comparison of the first area and the second area are available from the management system for access by laboratory personnel.

* * * * *